US009964504B2

United States Patent
Brookes et al.

(10) Patent No.: US 9,964,504 B2
(45) Date of Patent: May 8, 2018

(54) TEST SYSTEM AND TEST METHOD

(71) Applicant: Rolls-Royce Mechanical Test Operations Centre GmbH, Blankenfelde-Mahlow (DE)

(72) Inventors: Stephan Peter Brookes, Berlin (DE); Barry Ward, Derbyshire (GB)

(73) Assignee: ROLLS-ROYCE DEUTSCHLAND LTD & CO KG, Blankenfelde-Mahlow (DE)

( * ) Notice: Subject to any disclaimer, the term of this patent is extended or adjusted under 35 U.S.C. 154(b) by 722 days.

(21) Appl. No.: 14/575,681

(22) Filed: Dec. 18, 2014

(65) Prior Publication Data

US 2015/0177169 A1 Jun. 25, 2015

(30) Foreign Application Priority Data

Dec. 19, 2013 (EP) ..................................... 13198627

(51) Int. Cl.
*G01N 25/72* (2006.01)
*G01M 99/00* (2011.01)
*G01N 3/60* (2006.01)
*G01N 3/08* (2006.01)

(52) U.S. Cl.
CPC .......... *G01N 25/72* (2013.01); *G01M 99/002* (2013.01); *G01N 3/08* (2013.01); *G01N 3/60* (2013.01); *G01N 2203/0222* (2013.01); *G01N 2203/0226* (2013.01); *G01N 2203/0228* (2013.01)

(58) Field of Classification Search
CPC ............ G01N 25/72; G01N 3/08; G01N 3/60; G01N 2203/0228; G01N 2203/0222; G01N 2203/0226; G01M 99/002

USPC .......................................................... 374/57
See application file for complete search history.

(56) References Cited

U.S. PATENT DOCUMENTS

| 4,346,754 A | * | 8/1982 | Imig | ........................ G01N 3/02 165/254 |
| 5,275,489 A | * | 1/1994 | Borneman | ............. G01N 25/72 250/334 |
| 5,567,051 A | | 10/1996 | Annati et al. | |
| 5,980,103 A | | 11/1999 | Ikuno et al. | |

(Continued)

FOREIGN PATENT DOCUMENTS

| JP | 58-100736 | 6/1983 |
| JP | 62-134540 | 6/1987 |

OTHER PUBLICATIONS

European Search Report dated May 23, 2014 for counterpart European Application No. 13198627.5.

*Primary Examiner* — Lisa Caputo
*Assistant Examiner* — Janice M Soto
(74) *Attorney, Agent, or Firm* — Shuttleworth & Ingersoll, PLC; Timothy J. Klima

(57) ABSTRACT

The invention relates to a test system for cooling and/or heating at least one test piece comprising a platform, at least one heating and/or cooling fluid providing means coupled to the platform, at least one position means for reproducibly fixing the relative position of the fluid providing means to the at least one test piece and wherein the at least one position means is connected to the platform, the platform comprising at least one fastening means, in particular two openings for releasable coupling the fluid providing means for an at least temporarily fixing of the relative position of the fluid proving means to the test piece. It also relates to a test method.

15 Claims, 4 Drawing Sheets

(56) References Cited

U.S. PATENT DOCUMENTS 6,246,969 B1 * 6/2001 Sinclair ............... G01M 99/002
  700/299
2014/0028013 A1 * 1/2014 Neiske ................. F02N 15/067
  285/18

* cited by examiner

TEST SYSTEM AND TEST METHOD

This application claims priority to European Patent Application EP13198627.5 filed Dec. 19, 2013, the entirety of which is incorporated by reference herein.

The invention deals with a test system and a test method according to the present disclosure.

Testing test pieces such as mechanical components is an integer part of the design process in machine construction. Apart from mere functional fitting and esthetic design it is necessary to test mechanical features of individual elements under environmental conditions similar to those characteristic in a desired working state. Moreover for the sake of device security and durability it is common practice to evaluate the long and short term device behavior in an environment similar to the corresponding envisioned operating point, under the influence of varying conditions falling within a desired operating parameter range or even under worst case conditions.

In existing prior art systems to simulate environmental temperature influences it is known to direct heating and/or cooling fluids by means of flexible plastic tubes towards a test piece. Thereby the fluid may additionally be guided through a corresponding nozzle to dissipate the fluid.

However, with the known systems a once installed test scenario usually deteriorates over time with respect to the initially set parameters.

The present invention therefore aims to provide test system in which a defined test scenario can be kept stable and is highly reproducible.

This problem is solved by a test system with features as disclosed herein. The test system for cooling and/or heating at least one test piece comprises a platform and at least one heating and/or cooling fluid providing means coupled to the platform. Furthermore, at least one position means is used for reproducibly fixing the relative position of the fluid providing means to the at least one test piece and wherein the at least one position means is connected to the platform, the platform comprising at least fastening means, in particular two openings for releasable coupling the fluid providing means for an at least temporarily fixing of the relative position of the fluid proving means to the test piece.

The fluid to thermally condition the test pieces can comprise hot or cool air, nitrogen or a liquid, preferably water or oil. The choice of the fluid and the flow conditions influences the heat transfer possible to the test piece.

In particular an embodiment can indicate the relative position of the position means, in particular in the at least two openings by at least one marking and/or grating. With a marking a user can visually determine the position along e.g. a scale. A grating also allows a tactile feedback where the at last one position means is positioned.

In a further embodiment the platform comprises a breakout section, preferably with a circular circumference for the test piece so that the at least one fluid providing means is positionable around the at least one test piece.

It is also possible that at least one position means is coupled to an opening being at least partially arc-shaped. The arc-shape allows the adjusting of the fluid flow to the test piece under a certain angle.

In a further embodiment the linear and/or angular position of at least one fluid pipe, especially the tip of the fluid pipe with respect to the position means is indicated by a marking and/or grating on the fluid pipe and/or the position means. The at least one fluid pipe can be e.g. swivel around an angle to allow a further adjustment and fixation of the position of the fluid flow to the at least one test piece.

The embodiments can comprise at least one fluid dissipating nozzle detachably or permanently coupled to the fluid providing means, in particular to the at least one fluid pipe. The nozzle allows the definition of a narrow or broad fluid scope of the fluid flow for the at least one test piece.

Since the relative position between the fluid flow and the at least one test piece is important, it is advantageous if the at least one fluid providing means is mounted to the at least one position means so that the linear distance to the test piece and/or the angular position of the fluid providing means can be adjusted and/or fixed. The adjusting and/or fixing of the spatial position of the nozzle and/or the fluid providing means can be performed by machine means. This allows a reproducible positioning of the fluid flow. This is in particular advantageous when the spatial position of the nozzle and/or of the fluid providing means is controllable in dependence of measurement, in particular temperature measurements taken by measuring means from the test piece. The position of the fluid flow can changed in accordance with measurements. The control of the flow of the heating and/or cooling fluid dissipated over a test piece can be achieved by at least one valve. In particular, this can be achieved by at least one automatic controlled valve.

The problem is also solved with a method with the features as disclosed herein.

For testing the at least one test piece under controlled thermal conditions the following step are performed:

a) at least one heating and/or cooling fluid providing means is coupled to a platform, b) the relative position of the fluid providing means to the test piece (1) is preferably releasably fixed with at least one position means, c) heating and/or cooling fluid is supplied to the test piece.

Using an embodiment of the method it is possible to supply the heating and/or cooling fluid to the at least one test piece so that a predetermined temporal temperature profile and/or a spatial temperature profile in the test piece is achieved. A temporal temperature profile might comprise a defined raise in the temperature of the test piece. A spatial temperature profile might comprise defined different temperatures in different parts of the test piece. Combinations of these profiles are also possible.

Exemplarily embodiments of the test system and the test methods are be described with reference to the accompanied drawings, in which FIG. 1 depicts a bottom view of the exemplary test system;

FIGS. 1 and 2 show an exemplary embodiment of a test system being used to supply a heating and/or cooling fluid on a test piece 1.

Figure 2:
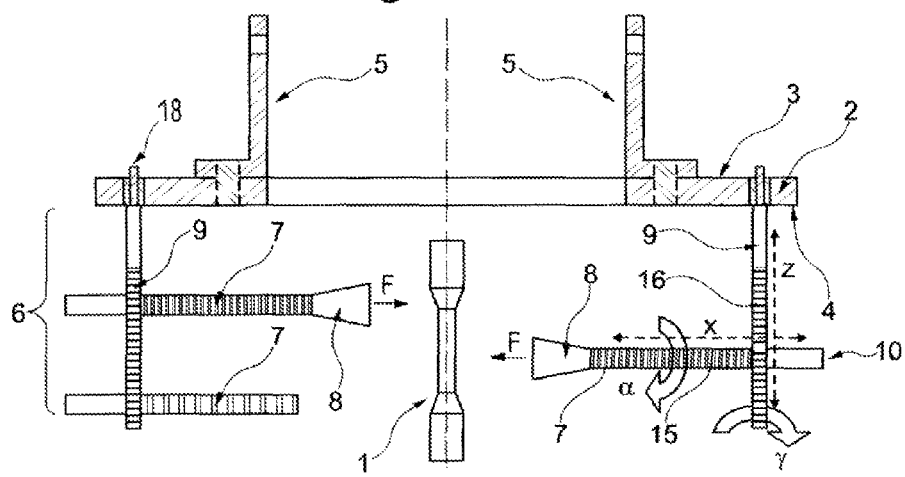
FIG. 2 depicts a side view of the same exemplary test system.

The test piece 1—as best shown in FIG. 2—is a test body having essentially a cylindrical form with different diameters. Standardized test pieces 1 like the one shown are routinely used in e.g. testing the tensile and/or compressive stress in metal materials. In other embodiments the test piece 1 could have a different form. In particular it is possible to use a real machine part as test piece 1 which will have a shape being very different from the standardized test piece 1 shown in FIG. 2. It is also possible to use more than one test piece 1 in one test system.

The mechanical behavior of the metal test piece 1 is to be investigated in the test system under certain, generally predetermined thermal conditions. For example a tensile and/or compressive stress measurement is performed at a prescribed temperature, e.g. room temperature or temperatures present in a working turbine (e.g. between 200 and 1700 K). With these temperature ranges nickel based alloys can be tested in temperature ranges of 200 K to 1700 K, titanium based alloys from 200 K to 850 K, intermetallics from 800 K to 1050 K, and steel alloys from 200 K to 1700 K.

The test system comprises a platform 2 that in this embodiment has an essentially circular, planar shape, with a circular outer circumference 12, the test piece 1 being positioned in a central breakout section 13 of the platform. In other alternatives the platform 2 can have other shapes like quadratic or rectangular. The platform 2 does not necessarily have to be a planar device. In yet other embodiments the platform can comprise a three dimensional structure which is sufficiently rigid to allow the positioning of the gas delivery as described below. The platform 2 in FIG. 1 is indicated by dashed lines to show the parts which are positioned above (see FIG. 2).

In an alternative embodiment the platform could be coupled with some walls or structures extending into the z-direction. The walls could comprise fluid providing means 6 to project towards the test piece 1.

Figure 1:
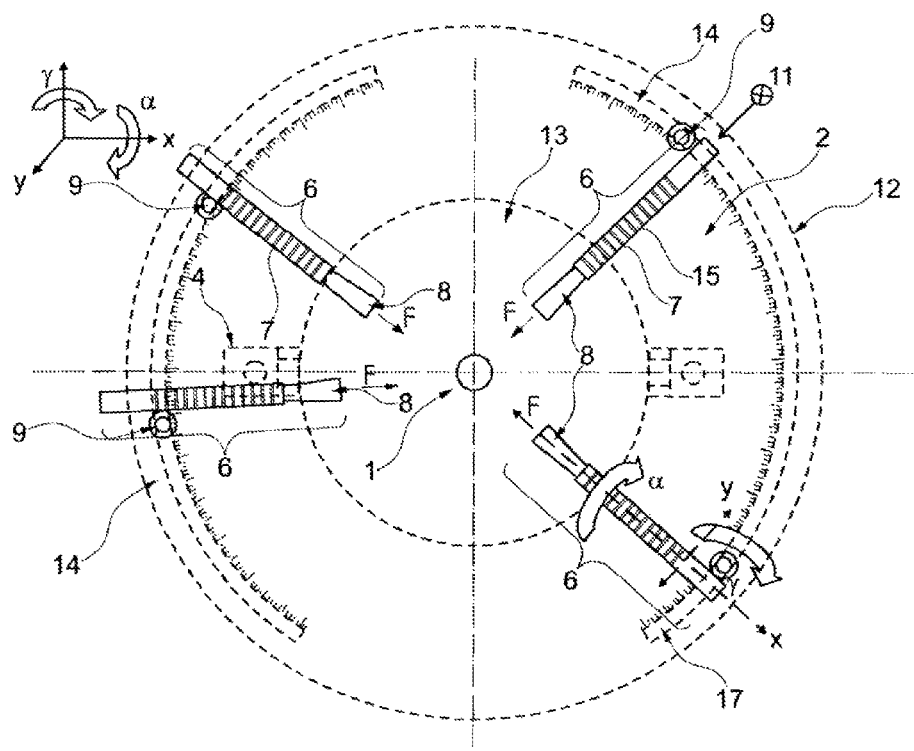

On a first surface 3 of the planar platform 2 shown in FIGS. 1 and 2 a set of supporting brackets serving as fixation means 5 adapted to be connected to a mechanical testing machine are positioned.

The planar platform 2 additionally comprises two arc shaped openings 14 allowing the attachment of heating and/or cooling fluid providing means 6. The openings 14 are one embodiment of a fastening means 14, i.e. means to which the fluid providing means 6 can be at least temporarily fixed. Alternative embodiments might use e.g. clamping devices attachable to the platform 2.

In the embodiment shown the fluid providing means 6 are positioned underneath the planar platform 2, i.e. they are mounted below a second surface 4 of the platform 2.

The openings 14 extend as arcs around a substantially part of the circular platform 2. This allows that the fluid providing means 6 can be positioned along the openings 14 to give an almost 360° to the test piece 1, i.e. nozzles 8 can be pointed from almost any direction to the test piece 1.

The fluid providing means 6 comprise fluid pipes 7 which are equipped at their one end with nozzles 8. Fluid inlets 10 are at the other ends of the fluid pipes 7. The nozzles 8 point towards the test piece 1 so that cooling and/or heating fluid can be discharged onto the test piece 1 to achieve a predetermined temperature or a predetermined time-dependent (temporal) and/or spatial temperature profile. The temporal profile would subject the test piece 1 to a certain time dependent temperature, e.g. a ramp function by increasing the temperature in a defined manner. Alternatively or additionally the temperature profile could be spatial (i.e. dependent on the location on the test piece 1). With such a profile different parts of the test piece 1 could be subjected to different temperatures. These temporal and spatial temperature profiles could be used in combination.

The fluid can be a gas like air or nitrogen (hot or cool) or a liquid like water or oil (hot or cool). The fluid is discharged, e.g. sprayed on the test piece 1. The fluid interacts with the test piece 1 to keep it a predetermined temperature or to realize a fluid influenced profile.

The fluid velocity and pressure depends on the material used for the fluid providing means 6. It is possible to apply a fluid with a 6 bar pressure through 8 mm diameter stainless steel fluid pipes 7.

The fluid providing means 6 are coupled to a position means 9 which is here is a threaded rod extended perpendicularly from end of position means 9 on which a nut and washer is screwed 18).

Figure 3:
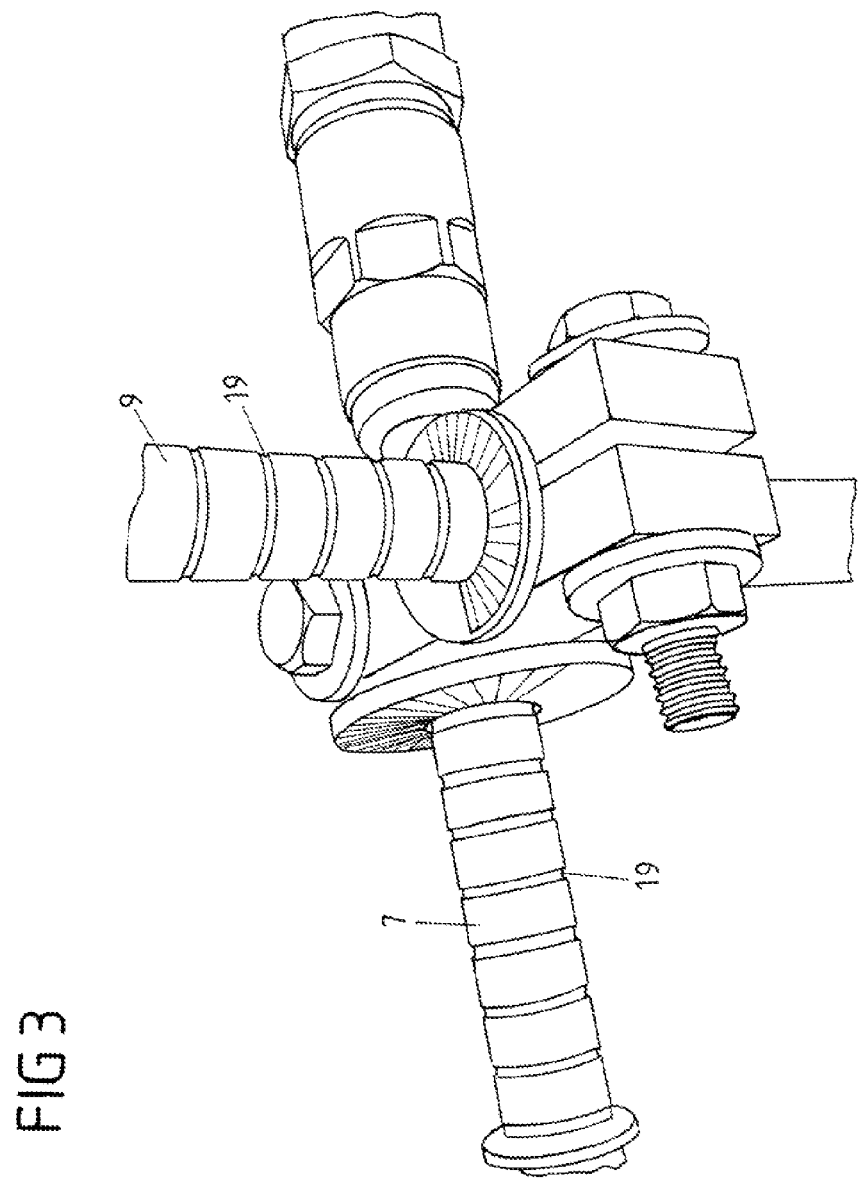
FIG. 3 shows a detail of the connection of a fluid pipe and a position means.

In FIG. 3 the connection between an essentially horizontal fluid pipe 7 with an essentially vertical position means 9 is shown. The fluid pipe 7 and the position means 9 comprise a plurality of grooves which provide a visual marking of the position and form locking elements to secure the linear position the fluid pipe 7 and the position means 9. Furthermore, on the tube pipe 7 and the positions means 7 angular markings are located to show the angular orientation.

The mounting of the fluid providing means 6 on the platform 2 allows a flexible, reproducible fixing of the position of fluid flows F (indicated by arrows in FIGS. 1 and 2) onto the test device 1. In FIGS. 1 and 2 the possible movements of the fluid providing means 6 relative to the test piece 1 are indicated. The position means 9 can be moved along the opening 14 (indicated by the direction y). In FIG. 1 it is shown that four fluid providing means point to the test piece 1 in different angles along the openings 14 onto the test piece 1, the longitudinal axis of the fluid providing means 6 (i.e. the nozzles 8) are all generally pointed towards the test piece 1 so that the fluid will hit the test piece 1 directly not tangentially.

If necessary the angle γ around the position means 9 can be adjusted which might be useful if the test piece 1 has a more extended or asymmetric shape than the test piece 1 shown in FIGS. 1 and 2. Furthermore, it is possible that the angle α, the rotation around the axis of the fluid tube 6 can be adjusted.

So the fluid providing means 6 can e.g. be moved up and down in z-direction (see FIG. 2) and/or in x-direction towards the test piece 1 or away from the test piece 1. Essentially it is possible to provide yaw, pitch and/or roll positioning for the nozzles 8, i.e. the fluid flows to the test piece 1.

It is also possible (but not shown in FIGS. 1 and 2) that the tubular part of the fluid providing means 6, i.e. the fluid pipe 7 can be tilted against the perpendicular position means 9 so that the fluid will be discharged onto the test piece from an angled direction.

To reproducibly position the fluid providing means 6 first markings 15 are located on the fluid pipes 7 indicating the position in x-direction and second markings 16 are located on the position means 9 indicating the position in z-direction. Third markings 17 are located next to the openings 14 to indicate the position of the fluid providing means 6 along the arc-shaped openings 14 (y-direction). The spacing of the markings 15, 16, 17 e.g. could be in steps of 1 mm or 5 mm, depending on the accuracy to be achieved. Alternatively or in addition to the markings 15, 16, 17 gratings could be used which would provide visual and mechanical (e.g. tactile) positioning information.

When the test setup of the test system is determined and e.g. an experiment has shown that the thermal conditioning of the test piece 1 is satisfactory, the spatial settings can be determined at the markings 15, 16, 17. So if the testing conditions need to be reproduced, the fluid providing means 6 can be positioned exactly as previously determined. This ensures the reproducibility of the testing.

In the shown embodiment the position means 9 with the attached parts allows the manual positioning in x-, y- and z-directions and the described angular positionings.

In alternative embodiments the position means 9 comprise a machine means, e.g. linear and/or angular drives with digital device used for measurement to position the fluid providing means 6 in a reproducible manner. The markings 15, 16, 17 could then allow a visual inspection. The machine means would keep track of the position by other means, e.g. by tracking the length of movements. Machine means and manual means can be used together or alternatively.

In the embodiment shown, the fluid flows F to at least one of the fluid providing means 6 can be controlled by at least one fluid flow influencing valve 11 which either regulates the fluid flows F to either an individual fluid pipe 7 or to a group of fluid 7 pipes commonly connected to a single valve.

The valves could comprise a solenoid valve operated by voltage signal, which regulates the fluid supply into the tubes.

The test system can comprise temperature measurement means, e.g. thermal camera to monitor the temperature of the test piece 1 during the test. A control device can use input from the temperature measurement means to adapt the flowrate and/or the temperature of the fluid through the nozzles 8 accordingly. If the control device knows the position of the fluid flows F to the test piece 1, the temperature and/or flowrate of the fluid can be adjusted individually for each fluid flow F allowing a differentiated thermal management of the test piece 1.

Figure 4:
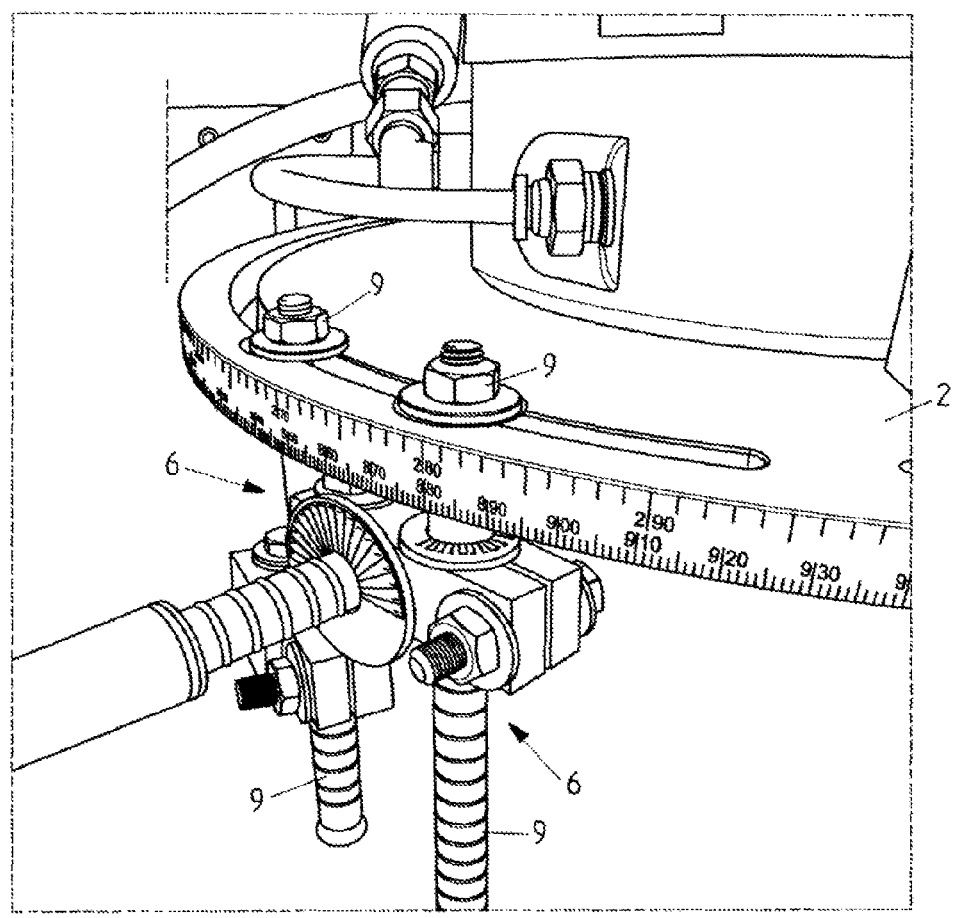
FIG. 4 shows a perspective side view of an embodiment of the exemplary test system.
Figure 5:
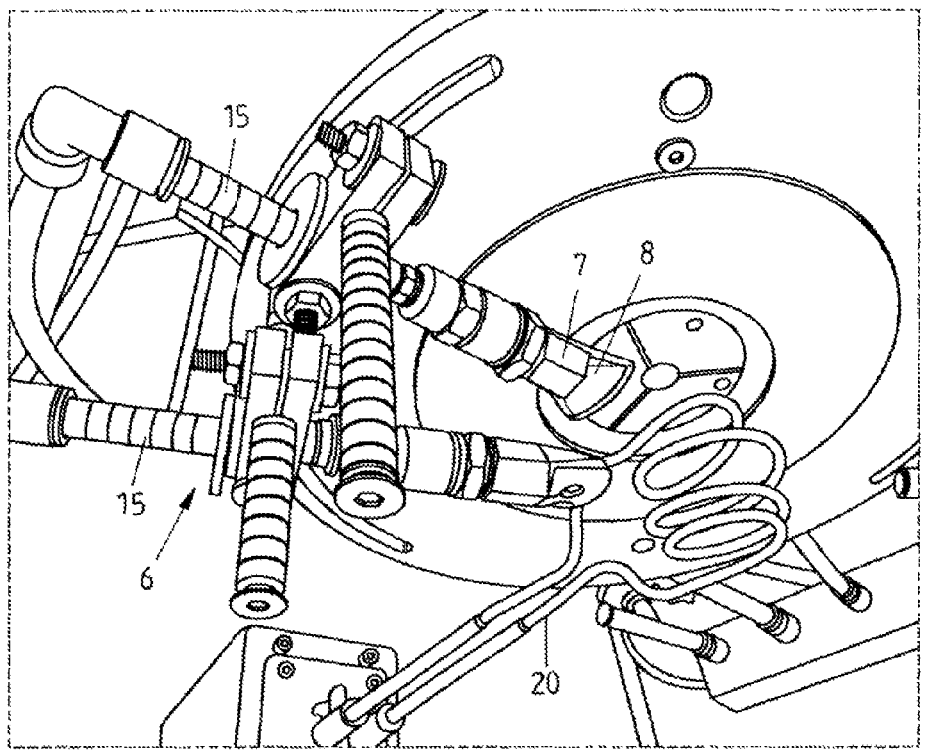
FIG. 5 shows a perspective view of area for the test piece.

In FIGS. 4 and 5 perspective views of embodiments also depicted in FIGS. 1 to 3 are shown. FIG. 4 shows a side view of the test system with two fluid providing means 6 (one is somewhat hidden from view) comprising a position mean 9 for vertically adjusting the fluid pipe 7 shown in FIG. 1 or 5. Around the rim of the platform 2 a scale an angular marking is positioned so that the angular position of the fluid providing means 6 can be accurately determined. The platform 2 comprises arc-like openings 14 in which the fluid providing means 6 be fastened e.g. by bolts. In alternative embodiments the platform 2 and/or the openings 14 can have a different shape. The fastening can also be designed different, e.g. a clamping mechanism could be used.

FIG. 5 shows also a perspective view as FIG. 4 but from a viewpoint further below. Here the two positioning means 9 with each one fluid pipe 7 and nozzle 8 can be seen. The nozzles 7 are directed towards the test piece 1 which is not shown here. The test piece 1 would be surrounded by an electrical heating coil 20.

With embodiments such as the exemplary ones shown in FIGS. 1 to 5 the at least one position means is connected to the platform 2, here circular shaped platform. The platform comprises fastening means, in particular two openings for releasable coupling the fluid providing means for an at least temporarily fixing of the relative position of the fluid proving means to the test piece. In the embodiments shown, the platform and the fluid providing means are connected with a nut-bolt connection. As mentioned above, other connections are possible in other embodiments.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims. All language of distinction and disparagement with respect to certain features is intended to indicate a lack of preference for those features, but not to exclude such from the scope of the disclosure entirely unless otherwise indicated. All methods described herein can be performed in any suitable order unless otherwise indicated herein or otherwise clearly contradicted by context. Various features of the various embodiments disclosed herein can be combined in different combinations to create new embodiments within the scope of the present disclosure. Any ranges given herein include any and all specific values within the range and any and all ranges within the given range.

TABLE OF REFERENCES 1 test piece
2 platform
3 first main surface
4 second main surface
5 fixation means adapted to statically connect the test system to a mechanic testing machine
6 fluid providing means (for cooling and/or heating fluid)
7 fluid pipe
8 nozzle
9 position means
10 cooling or heating fluid inlet
11 fluid flow influencing valve
12 circumference defining the outer shape of the solid platform
13 breakout section
14 fastening means, openings
15 first marking
16 second marking
17 third marking
18 fixation nut for position 9
19 groove
20 heating coil
F fluid flow
X representing a translational degree of freedom allowing the movement of the fluid pipe tip (nozzle) along the axis of the fluid pipe
Y representing a translational degree of freedom allowing the movement of the position means along the perimeter of the solid platform
Z representing a translational degree of freedom allowing the movement of the fluid pipe along an axis of the position means
α representing a rotational degree of freedom allowing the rotation of the fluid pipe around its own axis
γ representing a rotational degree of freedom allowing the rotation of the heating and/or cooling fluid providing means around the fixation axis of the intermediate fixation element

The invention claimed is:

1. A test system for at least one chosen from cooling and heating a test piece comprising:
   a platform,
   a fluid conduit for providing at least one chosen from a heating fluid and a cooling fluid,
   a positioning device coupling the fluid conduit to the platform for adjustably fixing a relative position of the fluid conduit with respect to the test piece; and
   wherein the platform comprises a fastening device including two openings and the positioning device is connected to the platform via at least one of the two openings for adjustably coupling the fluid conduit to the platform for providing the adjustable fixing;
   wherein at least one chosen from the platform and the positioning device includes at least one chosen from a marking and a grating for indicating a relative position of the position device with respect to the at least one of the two openings.

2. The test system according to claim 1, wherein the at least one chosen from the heating fluid and the cooling fluid comprises at least one chosen from hot air, cool air, nitrogen and a liquid.

3. The test system according to claim 2, wherein the liquid is water or oil.

4. The test system according to claim 1, wherein the platform comprises an opening including a circular circumference in which the test piece is positionable to leave a portion of the test piece open to the fluid conduit.

5. The test system according to claim 1, wherein the at least one chosen from the two openings includes an arc-shaped portion.

6. The test system according to claim 1, and further comprising a fluid dissipating nozzle coupled to the fluid conduit.

7. The test system according to claim 6, and further comprising a machine device for adjusting or fixing a spatial position of at least one chosen from the nozzle and the fluid conduit.

8. The test system according to claim 7, and further comprising a temperature measurement sensor for measuring a temperature of the test piece and controlling the adjusting or fixing by the machine device based on the measured temperature of the test piece.

9. The test system according to claim 1, wherein the fluid conduit is adjustably mounted to the positioning device to adjustably fix at least one chosen from a linear distance of the fluid conduit to the test piece and an angular position of the fluid conduit relative to the test piece.

10. The test system according to claim 1, and further comprising a valve for adjusting a flow of the at least one chosen from the heating fluid and the cooling fluid.

11. The test system according to claim 10, wherein the valve is a manually controlled valve.

12. The test system according to claim 10, wherein the valve is an automatically controlled valve.

13. A method for testing a test piece under controlled thermal conditions, wherein:
    a) providing a fluid conduit for providing at least one chosen from a heating fluid and a cooling fluid and providing that the fluid conduit is coupled to a platform,
    b) releasably fixing a relative position of the fluid conduit with respect to the test piece with a positioning device wherein the positioning device is connected to the platform, the platform comprising a fastening device including two openings for releasably coupling the fluid conduit for providing the releasable fixing,
    c) supplying the at least one chosen from the heating fluid and the cooling fluid through the fluid conduit to the test piece,
    providing at least one chosen from the fluid conduit and the position device with at least one chosen from a marking and a grating for indicating at least one chosen from a linear position and an angular position of the fluid conduit with respect to the position device and using the at least one chosen from the linear position and the angular position to accurately position the fluid conduit with respect to the position device.

14. The method according to claim 13, and further comprising achieving at least one chosen from a predetermined temperature profile and a spatial temperature profile in the test piece via the supplying the at least one chosen from the heating fluid and the cooling fluid through the fluid conduit to the test piece.

15. A test system for at least one chosen from cooling and heating a test piece comprising:
    a platform,
    a fluid conduit for providing at least one chosen from a heating fluid and a cooling fluid,
    a positioning device coupling the fluid conduit to the platform for adjustably fixing a relative position of the fluid conduit with respect to the test piece; and
    wherein the platform comprises a fastening device including two openings and the positioning device is connected to the platform via at least one of the two openings for adjustably coupling the fluid conduit to the platform for providing the adjustable fixing;
    wherein at least one chosen from the fluid conduit and the position device includes at least one chosen from a marking and a grating for indicating at least one chosen from a linear position and an angular position of the fluid conduit with respect to the position device.

* * * * *